US011253841B2

United States Patent
Faungnawakij et al.

(10) Patent No.: US 11,253,841 B2
(45) Date of Patent: Feb. 22, 2022

(54) COPPER ALUMINIUM OXIDE CATALYST FOR PREPARING FURFURYL ALCOHOL FROM FURFURAL AND A PREPARATION OF SAID CATALYST

(71) Applicant: PTT Global Chemical Public Company Limited, Bangkok (TH)

(72) Inventors: Kajornsak Faungnawakij, Pathum Thani (TH); Chuleeporn Luadthong, Pathum Thani (TH); Siripit Songtawee, Pathum Thani (TH); Chalita Ratanatawanate, Pathum Thani (TH)

(73) Assignee: PTT GLOBAL CHEMICAL PUBLIC COMPANY LIMITED, Bankok (TH)

( * ) Notice: Subject to any disclaimer, the term of this patent is extended or adjusted under 35 U.S.C. 154(b) by 566 days.

(21) Appl. No.: 16/305,935

(22) PCT Filed: May 30, 2017

(86) PCT No.: PCT/TH2017/000042
§ 371 (c)(1),
(2) Date: Nov. 30, 2018

(87) PCT Pub. No.: WO2017/209705
PCT Pub. Date: Dec. 7, 2017

(65) Prior Publication Data
US 2020/0324275 A1    Oct. 15, 2020

(30) Foreign Application Priority Data
May 31, 2016    (TH) ................... 1601003159

(51) Int. Cl.
*B01J 23/72*  (2006.01)
*B01J 6/00*   (2006.01)
(Continued)

(52) U.S. Cl.
CPC ............... *B01J 23/72* (2013.01); *B01J 6/001* (2013.01); *B01J 23/005* (2013.01); *B01J 37/08* (2013.01);
(Continued)

(58) Field of Classification Search
CPC . B01J 23/72; B01J 6/001; B01J 23/005; B01J 37/08; C07D 307/44
See application file for complete search history.

(56) References Cited

U.S. PATENT DOCUMENTS

2014/0303420 A1    10/2014 Holmes Spangsberg et al.

FOREIGN PATENT DOCUMENTS

| CN | 103877977 A | 6/2014 |
| CN | 105148912 A | 12/2015 |

(Continued)

OTHER PUBLICATIONS

International Search Report dated Nov. 24, 2017; International Application No. PCT/TH2017/000042; International Filing Date: May 30, 2017; 4 pages.

(Continued)

*Primary Examiner* — James A Fiorito
(74) *Attorney, Agent, or Firm* — Blank Rome LLP

(57) ABSTRACT

The present invention relates to a copper aluminium oxide catalyst for preparing a furfuryl alcohol from a furfural, comprising a copper-alumina spinel structure and having surface area in the range from 0.5 to 5 m$^2$/g; wherein said catalyst is prepared from a process comprising the following steps: (i) dissolving copper salt and aluminium salt in a solvent; (ii) adding organic acid into mixture obtained from step (i); (iii) heating mixture obtained from step (ii) at the temperature higher than 150° C. until said mixture is combusted into solid; and (iv) calcining the solid obtained from step (iii) at the temperature in the range from 700 to 1,000°

(Continued)

Diffraction angle 2 degree theta    Diffraction angle 2 degree theta

C. The catalyst according to the invention gives a high conversion of furfural to furfuryl alcohol and high furfuryl alcohol yield.

24 Claims, 2 Drawing Sheets

(51) Int. Cl.
  *B01J 23/00* (2006.01)
  *B01J 37/08* (2006.01)
  *C07D 307/44* (2006.01)
  *B01J 35/10* (2006.01)

(52) U.S. Cl.
  CPC ......... *C07D 307/44* (2013.01); *B01J 35/1009* (2013.01); *B01J 35/1038* (2013.01); *B01J 35/1042* (2013.01)

(56) References Cited

FOREIGN PATENT DOCUMENTS

| | | |
|---|---|---|
| GB | 2143524 A | 2/1985 |
| GB | 2482887 A | 2/2012 |

OTHER PUBLICATIONS

Written Opinion dated Nov. 24, 2017; International Application No. PCT/TH2017/000042; International Filing Date: May 30, 2017; 7 pages.

Li, G.J. et al., Catalytic characteristics of spinel CuM2O4 (M=Al, Fe, Cr) for the steam reforming of methanol. Journal of Fuel Chemistry and Technology, Dec. 3, 2012, vol. 40, No. 12, pp. 1466-1471. [Retrieved on Nov. 17, 2017] <DOI:10.3969/J.ISSN.0253-2409.2012.12.009>(see whole document—in particular Abstract, Section 1.2, Figure 1 and Table 1).

Patrick, V. et al., Structure and Reduction Of Mixed Copper-Aluminum Oxide, Journal of the American Ceramic Society, Feb. 28, 1990, vol. 73, No. 2, pp. 358-369. [Retrieved on Nov. 17, 2017] <DOI: 10.1111/J.1151-2916.1990.TB06519.X> (See Sampl A1 in Table 1).

Salavati-Niasari, M. et al., Synthesis and characterization of spinel-type CuAl2O4, nanocrystalline by modified sol-gel method. Journal of Sol-Gel Science and Technology, Mar. 17, 2009, vol. 51, No. 1, pp. 48-52. [Retrieved on Nov. 17, 2017] <DOI: 10.1007/S10971-009-1940-3> (See Section 2.1).

Wang, Y. et al., Preparation and photoelectric properties of spinel MAl2)4 (M=Cu, Ni) nanopowders. Journal of Dalian Polytechnic University, May 31, 2012, vol. 31, No. 3, pp. 187-190. [Retrieved on Nov. 17, 2017] <DOI: 10.3969/J.ISSN.1674-1404.2012.03.009> (see Section 1.1).

Nassar, M. Y. et al., A novel synthetic route for magnesium aluminate (MgAl2O4) nanoparticles using sol-gel auto combustion method and their photocatalytic properties. Spectrochima Acta. Part A: Molecular and Biomolecular Spectroscopy. Apr. 19, 2014, vol. 131, pp. 329-334. [Retrieved on Nov. 17, 2017] <DOI:10.1016/J.SAA.2014.04.040> (see Experimental Section—One step synthesis of spinel MgAl2O4 photocatalyst).

Li, W. et al., Synthesis and characterization of nanocrystalline CoAl2O4 spinel powder by low temperature combustion. Journal of the European Ceramic Society, Apr. 17, 2003, vol. 23, No. 13, pp. 2289-2295 [Retrieved on Nov. 17, 2017] <DOI: 10.1016/S095-2219(03)00081-5> (see Section 2. Experimental).

English translation; Chinese Publication CN103877977; Published Jun. 25, 2014. 7 pages.

English translation; Chinese Publication No. CN105148912; Published Dec. 16, 2015; 11 pages.

COPPER ALUMINIUM OXIDE CATALYST FOR PREPARING FURFURYL ALCOHOL FROM FURFURAL AND A PREPARATION OF SAID CATALYST

RELATED APPLICATIONS

This application is a U.S. national phase application of International Application No. PCT/TH2017/000042, filed May 30, 2017; which application claims priority to Thailand Application No. 1601003159, filed May 31, 2016. Each of the above-identified related applications are incorporated by reference.

TECHNICAL FIELD OF THE INVENTION

The present invention relates to the field of chemistry, in particular, a copper aluminium oxide catalyst for preparing furfuryl alcohol and preparation process for said catalyst.

BACKGROUND OF THE INVENTION

At present, the use of agricultural biomass in the production of fuel, energy, and chemicals, biochemical industry, has gained many attentions because of concerns in petroleum resources in both crude oil and natural gas that is about to be finished. Moreover, the use of agricultural biomass can help to reduce environmental problems such as reducing the release of greenhouse gas in to atmosphere.

Lignocellulosic biomass comprises polysaccharides i.e. cellulose, hemicellulose, and lignin as main components. When lignocellulosic biomass is decomposed by chemical and biochemical processes, the high value chemicals are obtained. One of the molecules that gain many attentions is furanic compound, especially furfural. When furfural is subjected to hydrogenation reaction, furfuryl alcohol is obtained. This is the important chemical that has been used in many industries such as lubricant oil, polymer resins, and textile, etc.

Generally, furfuryl alcohol can be prepared by subjecting furfural to hydrogenation reaction under catalytic condition. However, apart from furfuryl alcohol, there are some other by-products obtained from this reaction such as furan and tetrahydrofurfuryl alcohol. Therefore, there are many attempts to research and development catalyst for improving selectivity of furfuryl alcohol. The conventional catalyst being used in the industry is copper-chromite compound which has selectivity of furfuryl alcohol more than 99% as been disclosed in patent document U.S. Pat. No. 4,251,396A.

However, said copper-chromite compound is highly toxic and becomes pollution. Therefore, there were continuous research and development of other non-chromium catalysts in order to avoid the use of highly toxic substance in the preparation of catalyst. Meanwhile, the obtained catalyst still can give high selectivity of furfuryl alcohol.

Patent document CN103007941 disclosed the preparation process of catalyst comprising copper oxide—silicon oxide for hydrogenation reaction of furfural. It was found that the catalyst according to said invention gave 99.5% conversion of furfural into product and 98.5% selectivity of furfuryl alcohol.

Patent document CN102603681 disclosed the production of furfuryl alcohol for hydrogenation reaction of furfural using copper-aluminum catalyst having transition metal selected from transition metal group VIB and VIII. The selectivity of furfuryl alcohol was 97%.

Patent document CN103285866 disclosed the preparation process of catalyst for hydrogenation reaction of furfural into furfuryl alcohol. Said catalyst comprises zinc oxide, nickel oxide, and copper. It was found that said catalyst gave 99% conversion of furfural and more than 97% selectivity of furfuryl alcohol.

The catalyst disclosed in above patent documents also had disadvantage in their stability and water resistance that can be contaminated in furfural because furfural precursor obtained from biomass might contain high amount of water, which could degrade the catalyst. This would give unwanted by-products and lower the selectivity of furfuryl alcohol. Moreover, the evaporation process of water from furfural was difficult. Therefore, the selection of water resistant catalyst is one of the important factors in order to reduce dehydration step prior the hydrogenation process of furfural which can reduce operation cost in commercial scale.

Publication of Catalyst Communications, 2012, Vol. 24, page 90-95 disclosed the preparation of copper aluminium oxide spinel ($CuAl_2O_4$ spinel) catalyst with nanocrystalline by sol-gel method. Said catalyst comprised 100% by weight of copper-alumina spinel structure with surface area of 42 $m^2/g$ and pore diameter of 27 nm. Said catalyst was used for a hydrogenolysis of glycerol and gave more than 90% conversion of glycerol into 1,2-propanediol and selectivity of 1,2-propanediol.

Patent document U.S. Pat. No. 4,386,219 disclosed hydrogenation process of aldehyde for the preparation of propanediol using copper aluminium oxide spinel catalyst prepared from co-precipitation. Said catalyst had surface area from 50 to 150 $m^2$ and pore diameter from 4,000 to 16,000 nm. Said catalyst gave 98% conversion of aldehyde into propanediol in continuous experiment.

It had been known that apart from composition of said catalyst, morphology of catalyst such as surface area and pore size also affected the reaction mechanism and its efficacy. Moreover, there were different specificities of each reaction. Therefore, catalysts according to above patents that were suitable for the formation reaction of propanediol might not suitable for hydrogenation reaction of furfural in order to give furfuryl alcohol product.

Chinese Journal of Catalysis, vol. 31, page 461-465 disclosed the preparation process of cooper magnesium aluminium oxide catalyst for hydrogenation reaction of furfural prepared from co-precipitation of Cu-containing hydrotalcite-type precursor. It was found that said catalyst gave 50% conversion of furfural and about 90% selectivity of furfuryl alcohol. However, the furfural conversion according to said document was not so high.

From said reason, this invention aims to develop the cooper aluminium oxide catalyst for preparing furfuryl alcohol from furfural that gives high conversion percentage of furfural into furfuryl alcohol and selectivity of furfuryl alcohol with stability and capability to resist water contaminated with precursors.

SUMMARY OF THE INVENTION

This invention aims to develop the copper aluminium oxide catalyst for producing furfuryl alcohol from a furfural, comprising a copper-alumina spinel structure and having surface area in the range from 0.5 to 5 $m^2/g$;

wherein said catalyst is prepared from a process comprising the following steps:

(i) dissolving mixture of copper salt and aluminium salt in a solvent;

(ii) adding organic acid into mixture obtained from step (i);

(iii) heating mixture obtained from step (ii) at the temperature higher than 150° C. until said mixture is combusted into solid; and (iv) calcining the solid obtained from step (iii) at the temperature in the range from 700 to 1,000° C.

(a) comparative catalyst 2 before exposed to hydrogen gas;

(b) comparative catalyst 2 after exposed to hydrogen gas;

(c) comparative catalyst 3 before exposed to hydrogen gas;

(d) comparative catalyst 3 after exposed to hydrogen gas;

(e) comparative catalyst 4 before exposed to hydrogen gas;

(f) comparative catalyst 4 after exposed to hydrogen gas;

(g) catalyst according to the invention A before exposed to hydrogen gas;

(h) catalyst according to the invention A after exposed to hydrogen gas;

(l) catalyst according to the invention B before exposed to hydrogen gas; and (j) catalyst according to the invention B after exposed to hydrogen gas.

Figure 2:
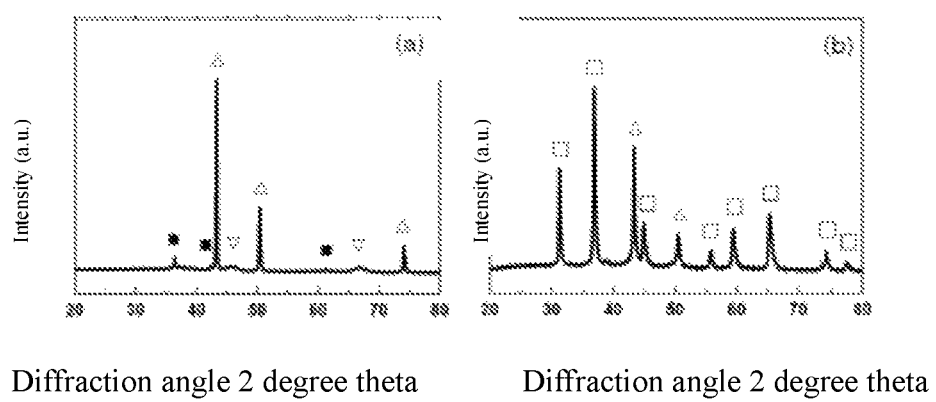

FIG. 2 shows the X-ray diffraction pattern of the comparative catalyst 2 and catalyst according to the invention B after producing furfuryl alcohol from furfural with water content of 30% by volume, CuO (♦), $Cu_2O$ (□), cubic $CuAl_2O_4$ (□), $Al_2O_3$ (Λ) uaz $Cu^0$ (Δ));

(a) comparative catalyst 2; and (b) catalyst according to the invention B.

DETAIL DESCRIPTION OF THE INVENTION

Definitions

Technical terms or scientific terms used here have definitions as by person skilled in the art unless stated otherwise.

Any tools, equipment, methods, or chemicals named here mean tools, equipment, methods, or chemicals being used commonly by person skilled in the art unless stated otherwise that they are tools, equipment, methods, or chemicals specific only in this invention.

Use of singular noun or singular pronoun with "comprising" in claims or specification means "one" and including "one or more", "at least one", and "one or more than one" too.

Throughout this application, term "about" means any number that appeared or showed here that could be varied or deviated from any error of equipment, method, or personal using said equipment or method including variations or deviations caused by reaction conditions of uncontrollable factors such as humid and temperature, etc.

Hereafter, invention specifications are shown without any purpose to limit any scope of the invention.

This invention relates to the copper aluminium oxide catalyst for producing furfuryl alcohol from a furfural, comprising a copper-alumina spinel structure and having surface area in the range from 0.5 to 5 $m^2/g$, wherein said catalyst is prepared from a process comprising the following steps:

(i) dissolving mixture of copper salt and aluminium salt in a solvent;

(ii) adding organic acid into mixture obtained from step (i);

(iii) heating mixture obtained from step (ii) at the temperature higher than 150° C. until said mixture is combusted into solid; and (iv) calcining the solid obtained from step (iii) at the temperature in the range from 700 to 1,000° C.

Preferable, the copper aluminium oxide catalyst comprises the copper-alumina spinel structure more than 85% wt, more preferably is in the range from 95 to 100% wt.

Preferable, the copper aluminium oxide catalyst has surface area in the range from 1 to 3 $m^2/g$.

In one embodiment, the copper aluminium oxide catalyst has pore diameter in the range from 3 to 20 nm, more preferably is from 10 to 15 nm.

In one embodiment, the copper aluminium oxide catalyst has pore volume in the range from 0.01 to 0.1 $cm^3/g$.

In one embodiment, the copper salt in step (i) is selected from copper nitrate, copper sulfate, copper acetate, or mixture thereof, preferably is copper nitrate.

In one embodiment, the aluminium salt in step (i) is selected from aluminium nitrate, aluminium sulfate, or mixture thereof, preferably is aluminium nitrate.

In one embodiment, the solvent in step (i) is selected from water, ethanol, or mixture thereof, preferably is water.

In one embodiment, the mole ratio of copper salt to aluminium salt in step (i) is in the range from 1:2 to 1:8, preferably is from 1:2 to 1:3.

In one embodiment, the organic acid in step (ii) is selected from citric acid, malic acid, oxalic acid, or mixture thereof, preferably is citric acid.

In one embodiment, the mole ratio of copper salt in step (i) to organic acid in step (ii) is in the range from 1:1 to 1:4, preferably is from 1:1 to 1:5.

In one embodiment, step (iii) is operated at the temperature from 170 to 350° C. for at least 1 hour.

In one embodiment, step (iv) is operated at the temperature from 800 to 950° C. for 1 to 8 hours, preferably is 3 to 5 hours.

In another embodiment, the present invention provides a use of the copper aluminium oxide catalyst for producing furfuryl alcohol from a furfural by contacting mixture of furfural, organic solvent and hydrogen gas with said catalyst. Preferable, the organic solvent may be selected from iso-propanol, ethanol, methanol, or mixture thereof. More preferable, the organic solvent is iso-propanol.

In one embodiment, the furfural comprising water between 0 to 30% by volume.

In one embodiment, said preparation process for furfuryl alcohol may be performed under suitable conditions for the reaction which may be operated in batch process or continuous process and may be performed at the temperature about 120 to 200° C., preferably is about from 150 to 190° C. It may be operated under total pressure from 20 to 40 bars, preferably is from 30 to 40 bars. The partial pressure of hydrogen gas is from 15 to 40 bars.

Generally, any person skilled in the art can adjust the reaction conditions in the preparation process for said furfuryl alcohol suitable to composition of precursor, reaction rate of catalyst, and reactor system.

Another objective of this invention is to disclose a preparation process for the copper aluminium oxide catalyst for preparing furfuryl alcohol from furfural, comprising the copper-alumina spinel structure and having surface area in the range from 0.5 to 5 $m^2/g$, wherein said process comprising the following steps;

(i) dissolving mixture of copper salt and aluminium salt in a solvent;

(ii) adding organic acid into mixture obtained from step (i);

(iii) heating mixture obtained from step (ii) at the temperature higher than 150° C. until said mixture is combusted into solid; and (iv) calcining the solid obtained from step (iii) at the temperature in the range from 700 to 1,000° C.

Preferable, said copper aluminium oxide catalyst comprises the copper-alumina spinel structure more than 85% wt, more preferably is in the range from 95 to 100% wt.

Preferable, said copper aluminium oxide catalyst has surface area in the range from 1 to 3 $m^2/g$.

Preferable, the copper aluminium oxide catalyst has pore diameter in the range from 3 to 20 nm, preferably is from 10 to 15 nm.

In one embodiment, said copper aluminium oxide catalyst has pore volume in the range from 0.01 to 0.1 $cm^3/g$.

In one embodiment, the copper salt in step (i) is selected from copper nitrate, copper sulfate, copper acetate, or mixture thereof, preferably is copper nitrate.

In one embodiment, the aluminium salt in step (i) is selected from aluminium nitrate, aluminium sulfate, or mixture thereof, preferably is aluminium nitrate.

In one embodiment, the solvent in step (i) is selected from water, ethanol, or mixture thereof, preferably is water.

In one embodiment, the mole ratio of copper salt to aluminium salt in step (i) is in the range from 1:2 to 1:8, preferably is from 1:2 to 1:3.

In one embodiment, the organic acid in step (ii) is selected from citric acid, malic acid, oxalic acid, or mixture thereof, preferably is citric acid.

In one embodiment, the mole ratio of copper salt in step (i) to organic acid in step (ii) is in the range from 1:1 to 1:4, preferably is from 1:1 to 1:5.

In one embodiment, step (iii) is operated at the temperature from 170 to 350° C. for at least 1 hour.

In one embodiment, step (iv) is operated at the temperature from 800 to 950° C. for 1 to 8 hours, preferably is operated for 3 to 5 hours.

The following part only aims to demonstrate the embodiments of this invention and not aims to limit the scope of this invention in any way.

Comparative Catalyst 1

The comparative catalyst 1 was the copper aluminium oxide catalyst prepared from citric acid complexation as the following details.

7.12 g of copper nitrate trihydrate and 22.97 g of aluminium nitrate were added into water at temperature 60° C. Said mixture was stirred until homogeneous. Then, 47.52 g of citric acid were added into said mixture and stirred at temperature 60° C. for 30 minutes until the homogenous solution was obtained. The pH was adjusted with ammonia to 14 and heated at temperature of 60-70° C. until the solution was viscos. The obtained substance was put in the oven at temperature 80° C. for 8 hours. The obtained solid was calcinated at temperature 900° C. for 3 hours with temperature rising rate of 200° C. per hour.

Comparative Catalyst 2

The comparative catalyst 2 was the copper aluminium oxide catalyst prepared from impregnation method as the following details.

3.94 g of copper nitrate were added 2.00 g of alumina supporter at temperature 60° C. and stirred for 2 hours. Then, the mixture was heated at temperature 100° C. for 8 hours and calcinated at temperature of 450° C. with temperature rising rate of 200° C. per hour.

Comparative Catalyst 3

The comparative catalyst 3 was the copper aluminium oxide catalyst prepared from citric acid complexation as the following details.

23.73 g of copper nitrate trihydrate and 76.56 g of aluminium nitrate were added into water at temperature about 60° C. Then, 88.70 g of citric acid were added into said mixture and stirred at temperature 100° C. Then, the mixture was continuously heated at temperature 300° C. until the solid substance was obtained.

Comparative Catalyst 4

The comparative catalyst 4 was the copper aluminium oxide catalyst prepared from citric acid complexation as the following details.

23.73 g of copper nitrate trihydrate and 76.56 g of aluminium nitrate were added into water at temperature about 60° C. Then, 88.70 g of citric acid were added into said mixture and stirred at temperature 100° C. Then, the mixture was continuously heated at temperature 300° C. until the solid substance was obtained. The obtained solid substance was calcinated at temperature 500° C. with the temperature rising rate 200° C. per hour.

Catalyst According to the Invention A

The catalyst according to the invention A is the copper aluminium oxide catalyst prepared according to the method described in the preparation of comparative sample 4 using the calcination temperature about 700° C.

Catalyst According to the Invention B

The catalyst according to the invention B is the copper aluminium oxide catalyst prepared according to the method described in the preparation of comparative sample 4 using the calcination temperature about 900° C.

The Preparation of Furfuryl Alcohol from Furfural with the Copper Aluminium Oxide Catalyst The copper aluminium oxide catalysts prepared by above methods were tested for their efficacy in the production of furfuryl alcohol from furfural according to the following details.

Before the reaction, the copper aluminium oxide catalyst was exposed to hydrogen gas for about 4 hours. The reaction was operated in 150 mL high pressure reactor. Then, 0.5 g of copper aluminium oxide catalyst and 3.1 mL of furfural in 21.9 mL isopropanol solvent were added into the reactor. Then, hydrogen gas was feed into the reactor for starting pressure at 40 bar and heated with stirring until the temperature reached at 170° C. Then, time was started to count. The reaction time was an 1 hour. Then, the reaction was stopped.

The obtained product was analyzed for amount of furfural and furfuryl alcohol using gas chromatography. The % conversion of furfural into furfuryl alcohol and % yield of obtained furfuryl alcohol were calculated from:

$$\text{\% conversion of furfural into furfuryl alcohol} = \frac{\text{mole of reacted furfural} \times 100}{\text{mole of starting furfural fed into the system}}$$

$$\text{\% yield of obtained furfuryl alcohol} = \frac{\text{mole of obtained furfural alcohol} \times 100}{\text{mole of starting furfural fed into the system}}$$

The followings are examples of property testing of the prepared copper aluminium oxide catalyst, wherein methods and equipment used in property testing were methods and equipment used generally and had no intention to limit the scope of the invention.

Surface area, pore diameter, and pore volume of the prepared catalyst could be determined by Brunauer, Emmett and Teller (BET) technique. The results are shown in Table 1.

Phase composition of the catalyst could be determined by X-ray diffraction technique. The results are also shown in Table 1, wherein the phase composition of $CuAl_2O_4$ means spinel structure in the catalyst.

Figure 1:
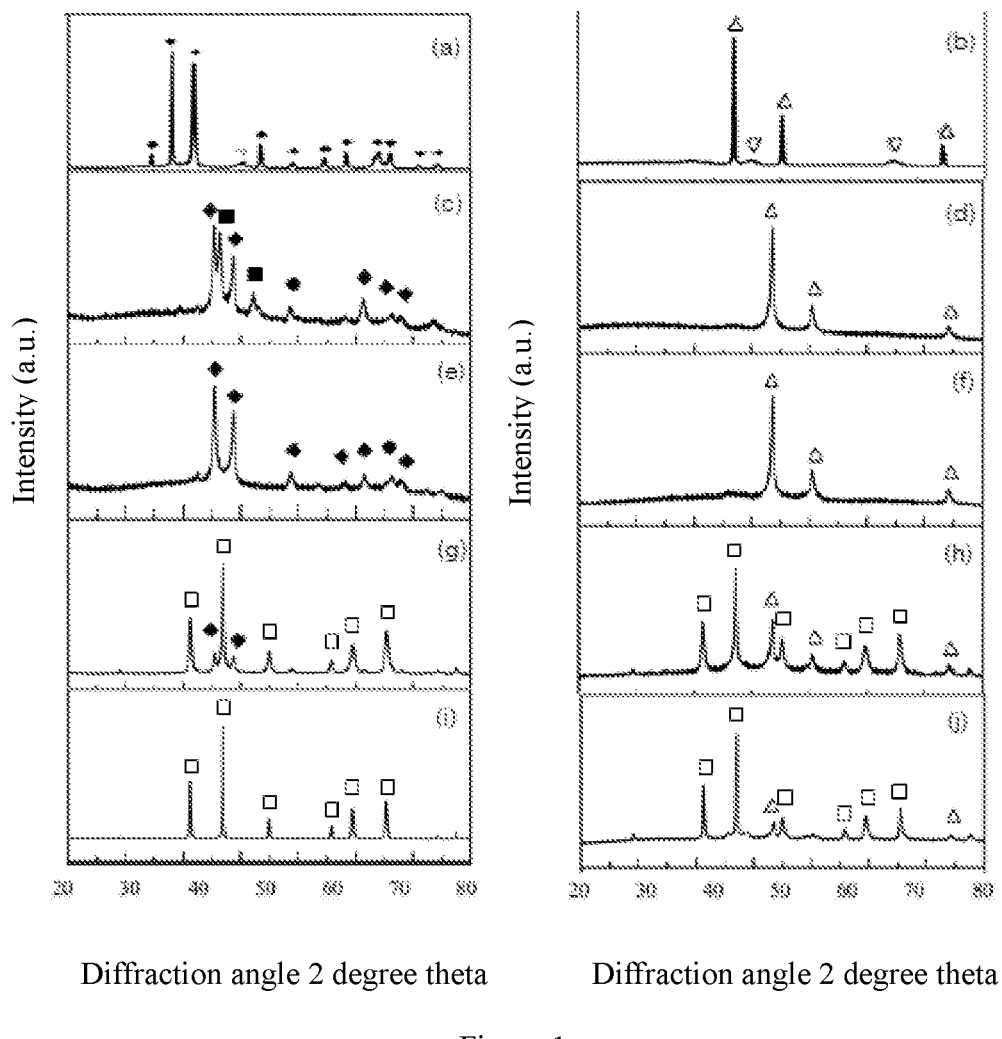
FIG. 1 shows the X-ray diffraction pattern of the copper aluminium oxide catalyst according to the invention and the comparative copper aluminium oxide catalyst before and after exposing to hydrogen gas for 4 hours, $CuAl_2O_4$ (□), CuO (♦), $Cu_2O$ (□), $Cu^0$ (Δ), and $Al_2O_3$ (∇)

The catalyst structure in both before and after exposed to hydrogen gas before being tested for the efficacy in preparation of furfuryl alcohol from furfural could be determined by X-ray diffraction technique. The results are shown in FIG. 1.

TABLE 1

Surface area, pore diameter, pore volume, and phase composition of the comparative catalysts and the catalysts according to the invention

| Catalyst | phase composition (%) | Surface area ($m^2/g$) | Pore diameter (nm) | Pore volume ($cm^3/g$) |
|---|---|---|---|---|
| Comparative catalyst 1 | $CuAl_2O_4$: 100 | 6.1 | 3.94 | 0.054 |
| Comparative catalyst 2 | CuO: 100 | 120-130 | 7.49 | 0.28-0.32 |
| Comparative catalyst 3 | CuO: 69.61 $Cu_2O$: 30.39 | 56.6 | 3.70 | 0.044 |
| Comparative catalyst 4 | CuO: 86.48 $Cu_2O$: 13.52 | 16.0 | 3.70 | 0.046 |
| Catalyst according to the invention A | CuO: 12.3 $CuAl_2O_4$: 87.7 | 4.2 | 3.65 | 0.097 |
| Catalyst according to the invention B | $CuAl_2O_4$: 100 | 1.8 | 11.35 | 0.021 |

TABLE 2

% conversion of furfural into furfuryl alcohol and % yield of obtained furfuryl alcohol of the comparative catalysts and the catalysts according to the invention

| Catalyst | % conversion of furfural into furfuryl alcohol | % yield of obtained furfuryl alcohol |
|---|---|---|
| Comparative catalyst 1 | 51.15 | 38.93 |
| Comparative catalyst 3 | 57.50 | 44.26 |
| Comparative catalyst 4 | 61.18 | 55.39 |
| Catalyst according to the invention A | 98.38 | 85.70 |
| Catalyst according to the invention B | 99.25 | 96.19 |

Table 2 shows % conversion of furfural into furfuryl alcohol and % yield of obtained furfuryl alcohol of the comparative catalyst and the catalyst according to the invention. It was found that the catalyst according to the invention A and B which prepared from the processes according to the invention comprising copper-alumina spinel structure and having surface area in the range from 0.5 to 5 $m^2/g$ gave higher % conversion of furfural into furfuryl alcohol and % yield of obtained furfuryl alcohol than the comparative catalysts. The catalyst according to the invention B that comprising 100% by weight of copper-alumina spinel structure had surface area about 1.8 $m^2/g$ and pore diameter about 11.35 nm, gave highest efficacy in the preparation of furfuryl alcohol from furfural.

Moreover, when comparing the comparative sample 1 and sample according to the invention B that comprising same structure composition of $CuAl_2O_4$ but with different morphologies which were surface area, pore size, and pore volume. The catalyst according to the invention B gave higher % conversion of furfural into furfuryl alcohol and % yield of obtained furfuryl alcohol than the comparative catalyst 1. This can be said that the morphology of the catalyst has many influences on the efficacy of the copper aluminium oxide catalyst for the preparation of furfuryl alcohol from furfural.

Influence of Water Quantity in Furfural on the Efficiency and Stability of the Copper Aluminium Oxide Catalyst In order to study the effect of the water contaminating in furfural precursor from biomass to efficiency and stability of the copper aluminium oxide catalyst in the preparation of furfuryl alcohol, the comparative catalysts and the catalysts according to the invention were brought into efficacy testing in the preparation of furfuryl alcohol according to the methods described above at starting hydrogen pressure about 20 bars and reaction time about 5 hours. Water was added into the reactors at 0, 10, 20, and 30% by volume. The results are shown in Table 3.

From Table 3, it was found that in the condition of water contamination in furfural at 10% by volume, when comparing comparative catalyst 2, 3, 4 and catalyst according to the invention B, the catalyst according to the invention B gave highest % conversion of furfural into furfuryl alcohol and % yield of obtained furfuryl alcohol. Moreover, when water quantity raised to 30% by volume, the comparative catalyst 2 gave much lower % conversion of furfural into furfuryl alcohol, whereas the catalyst according to the invention B gave little lower % conversion of furfural into furfuryl alcohol. The % yield of obtained furfuryl alcohol from the comparative catalyst 2 started to reduce clearly when water was contaminated at 20% by volume, whereas in the catalyst according to the invention B, the % yield of obtained furfuryl alcohol started to reduce clearly when water was contaminated at 30% by volume.

When studying in structure of the comparative catalyst 2 and the catalyst according to the invention B subjected to the preparation process of furfuryl alcohol from furfural contaminated with water at 30% by volume using X-ray diffraction technique. The results are shown in FIGS. 2 (a) and (b) respectively. It was found that the structure of the comparative catalyst 2 had new crystal plane at the position of copper (I) oxide ($Cu_2O$) plane because copper metal was oxidized by oxygen in water molecule and yielded copper (I) oxide. The said plane reduced the efficacy of the catalyst, whereas said copper (I) oxide plane was not found in the catalyst according to the invention B.

From the results above, it was found that the catalyst according to the invention B was stable and remained high efficacy in the preparation of furfuryl alcohol from furfural even in the condition of furfural containing water.

TABLE 3

% conversion of furfural into furfuryl alcohol and % yield of obtained furfuryl alcohol of the catalysts according to the invention and the comparative catalysts in processes that contained high amount of water

| Catalyst | % by volume of water | % conversion of furfural into furfuryl alcohol | % yield of obtained furfuryl alcohol |
|---|---|---|---|
| Comparative catalyst 2 | 0 | 98.74 | 92.84 |
| | 10 | 98.01 | 89.04 |
| | 20 | 83.77 | 57.74 |
| | 30 | 58.98 | 11.66 |

TABLE 3-continued

% conversion of furfural into furfuryl alcohol and % yield of obtained furfuryl alcohol of the catalysts according to the invention and the comparative catalysts in processes that contained high amount of water

| Catalyst | % by volume of water | % conversion of furfural into furfuryl alcohol | % yield of obtained furfuryl alcohol |
|---|---|---|---|
| Comparative catalyst 3 | 10 | 45.29 | 16.86 |
| Comparative catalyst 4 | 10 | 43.98 | 35.73 |
| Catalyst according to the invention B | 0 | 98.69 | 98.60 |
|  | 10 | 99.16 | 94.28 |
|  | 20 | 93.37 | 79.25 |
|  | 30 | 90.29 | 23.58 |

Effect of the Reaction Solvents to % Conversion of Furfural into Furfuryl Alcohol and % Yield of Obtained Furfuryl Alcohol In order to study the effect of solvent in the conversion of furfural into furfuryl alcohol, the catalyst according to the invention B was brought into the preparation of furfuryl alcohol according to the method described above using isopropanol and tetrahydrofuran as solvents. The results are shown in table 4.

From table 4, it was found that isopropanol gave higher % conversion of furfural into furfuryl alcohol and % yield of obtained furfuryl alcohol than tetrahydrofuran.

TABLE 4

% conversion of furfural into furfuryl alcohol and % yield of obtained furfuryl alcohol when isopropanol and tetrahydrofuran were used as solvent

| Solvent | % conversion of furfural into furfuryl alcohol | % yield of obtained furfuryl alcohol |
|---|---|---|
| Isopropanol | 99.25 | 96.19 |
| Tetrahydrofuran | 57.05 | 53.56 |

BEST MORE OF CARRYING OUT THE INVENTION

Best mode or preferred embodiment of the invention is as provided in the detail description of the invention.

The invention claimed is:

1. A copper aluminium oxide catalyst for producing furfuryl alcohol from a furfural, comprising a copper-alumina spinel structure and having surface area in the range from 0.5 to 5 m$^2$/g;
   wherein said catalyst is prepared from a process comprising the following steps:
   (i) dissolving copper salt and aluminium salt in a solvent;
   (ii) adding organic acid into mixture obtained from step (i);
   (iii) heating mixture obtained from step (ii) at the temperature higher than 150° C. until said mixture is combusted into solid; and
   (iv) calcining the solid obtained from step (iii) at the temperature in the range from 700 to 1,000° C.

2. The copper aluminium oxide catalyst according to claim 1, wherein said catalyst comprising the copper-alumina spinel structure in the range from 95 to 100% wt.

3. The copper aluminium oxide catalyst according to claim 1, wherein said catalyst has surface area in the range from 1 to 3 m$^2$/g and has pore diameter in the range from 10 to 15 nm.

4. The copper aluminium oxide catalyst according to claim 1, wherein said catalyst has pore volume in the range from 0.01 to 0.1 cm$^3$/g.

5. The copper aluminium oxide catalyst according to claim 1, wherein copper salt in step (i) is selected from copper nitrate, copper sulfate, copper acetate, or mixture thereof and aluminium salt in step (i) is selected from aluminium nitrate, aluminium sulfate, or mixture thereof.

6. The copper aluminium oxide catalyst according to claim 1, wherein the solvent in step (i) is selected from water, ethanol, or mixture thereof.

7. The copper aluminium oxide catalyst according to claim 1, wherein the mole ratio of copper salt to aluminium salt in step (i) is in the range from 1:2 to 1:8.

8. The copper aluminium oxide catalyst according to claim 1, wherein the organic acid in step (ii) is selected from citric acid, malic acid, oxalic acid, or mixture thereof.

9. The copper aluminium oxide catalyst according to claim 1, wherein the mole ratio of copper salt in step (i) to organic acid in step (ii) is in the range from 1:1 to 1:4.

10. The copper aluminium oxide catalyst according to claim 1, wherein step (iii) is operated at the temperature from 170 to 350° C. and operated for at least 1 hour.

11. The copper aluminium oxide catalyst according to claim 1, wherein step (iv) is operated at the temperature from 800 to 950° C. and operated for 1 to 8 hours.

12. A use of the copper aluminium oxide catalyst according to claim 1 for preparing the furfuryl alcohol from a furfural by contacting mixture of furfural, organic solvent and hydrogen gas with said catalyst.

13. The use of the copper aluminium oxide catalyst according to claim 12, wherein furfural comprising water between 0 to 30% by volume.

14. A preparation process for the copper aluminium oxide catalyst for preparing furfuryl alcohol from furfural, comprising the copper-alumina spinel structure and having surface area in the range from 0.5 to 5 m$^2$/g, wherein said process comprising the following steps;
   (i) dissolving mixture of copper salt and aluminium salt in a solvent;
   (ii) adding organic acid into mixture obtained from step (i);
   (iii) heating mixture obtained from step (ii) at the temperature higher than 150° C. until said mixture is combusted into solid; and
   (iv) calcining the solid obtained from step (iii) at the temperature in the range from 700 to 1,000° C.

15. The copper aluminium oxide catalyst according to claim 14, wherein said catalyst comprising the copper-alumina spinel structure in the range from 95 to 100% by weight.

16. The preparation process for the copper aluminium oxide catalyst according to claim 14, wherein said catalyst has surface area in the range from 1 to 3 m$^2$/g and pore diameter in the range from 10 to 15 nm.

17. The preparation process for the copper aluminium oxide catalyst according to claim 14, wherein said catalyst has pore volume in the range from 0.01 to 0.1 cm$^3$/g.

18. The preparation process for the copper aluminium oxide catalyst according to claim 14, wherein copper salt in step (i) is selected from copper nitrate, copper sulfate, copper acetate, or mixture thereof and aluminium salt in step (i) is selected from aluminium nitrate, aluminium sulfate, or mixture thereof.

19. The preparation process for the copper aluminium oxide catalyst according to claim 14, wherein the solvent in step (i) is selected from water, ethanol, or mixture thereof.

20. The preparation process for the copper aluminium oxide catalyst according to claim 14, wherein the mole ratio of copper salt to aluminium salt in step (i) is in the range from 1:2 to 1:8.

21. The preparation process for the copper aluminium oxide catalyst according to claim 14, wherein the organic acid in step (ii) is selected from citric acid, malic acid, oxalic acid, or mixture thereof.

22. The preparation process for the copper aluminium oxide catalyst according to claim 14, wherein the mole ratio of copper salt in step (i) to organic acid in step (ii) is in the range from 1:1 to 1:4.

23. The preparation process for the copper aluminium oxide catalyst according to claim 14, wherein step (iii) is operated at the temperature from 170 to 350° C. and operated for at least 1 hour.

24. The preparation process for the copper aluminium oxide catalyst according to claim 14, wherein step (iv) is operated at the temperature from 800 to 950° C. and operated for 1 to 8 hours.

* * * * *